United States Patent [19]

Silber et al.

[11] Patent Number: 5,342,331

[45] Date of Patent: Aug. 30, 1994

[54] TOXICITY RESISTANT TAMPON STRUCTURE

[76] Inventors: Arthur L. Silber, 543 Dobbins Ave., San Gabriel, Calif. 91775; Raymond C. Ng, 1737 Oak Grove, San Marino, Calif. 91108; James C. Caillouette, 685 Oak Knoll Cir., Pasadena, Calif. 91106

[21] Appl. No.: 2,642

[22] Filed: Jan. 11, 1993

[51] Int. Cl.⁵ .................. A61F 13/20; A61F 13/34
[52] U.S. Cl. .................. 604/330; 604/385.1; 604/904
[58] Field of Search .......... 604/385.1, 904, 55, 604/330, 354, 17, 14; 128/769

[56] References Cited

U.S. PATENT DOCUMENTS

| | | |
|---|---|---|
| 1,996,242 | 4/1935 | Hagedorn ................ 604/330 |
| 2,355,628 | 8/1944 | Calhoun . |
| 2,386,590 | 10/1945 | Calhoun . |
| 3,404,682 | 10/1968 | Waldron . |
| 3,491,758 | 1/1970 | Mullan . |
| 3,595,236 | 7/1971 | Corrigan et al. . |
| 3,626,942 | 12/1971 | Waldron . |
| 3,683,915 | 8/1972 | Voss . |
| 3,706,311 | 12/1972 | Kokx et al. . |
| 3,712,305 | 1/1973 | Wennerblom et al. . |
| 4,232,673 | 11/1980 | Bucalo ................ 128/769 |
| 4,286,594 | 9/1981 | Cunningham ............ 604/904 X |
| 4,857,044 | 8/1989 | Lennon . |

FOREIGN PATENT DOCUMENTS

| | | | |
|---|---|---|---|
| 1123155 | 5/1982 | Canada ................ 604/904 |
| 0753294 | 7/1956 | United Kingdom ........ 604/904 |

*Primary Examiner*—Randall L. Green
*Assistant Examiner*—D. Willse
*Attorney, Agent, or Firm*—William W. Haefliger

[57] ABSTRACT

A flow-controlling tampon, comprising a generally upright elongated sheath structure having an open upper end and a closed lower end, the upper end sized to fit about the cervix an inner, elongated, flow-control tube extending generally upright within the sheath, the tube having an upper open end to receive flow via the upper open end of the sheath, and the flow-control tube having lower opening structure to pass flow from the tube into the lower interior of the sheath to gradually collect upwardly from the lower interior of the sheath, and about the control tube.

12 Claims, 2 Drawing Sheets

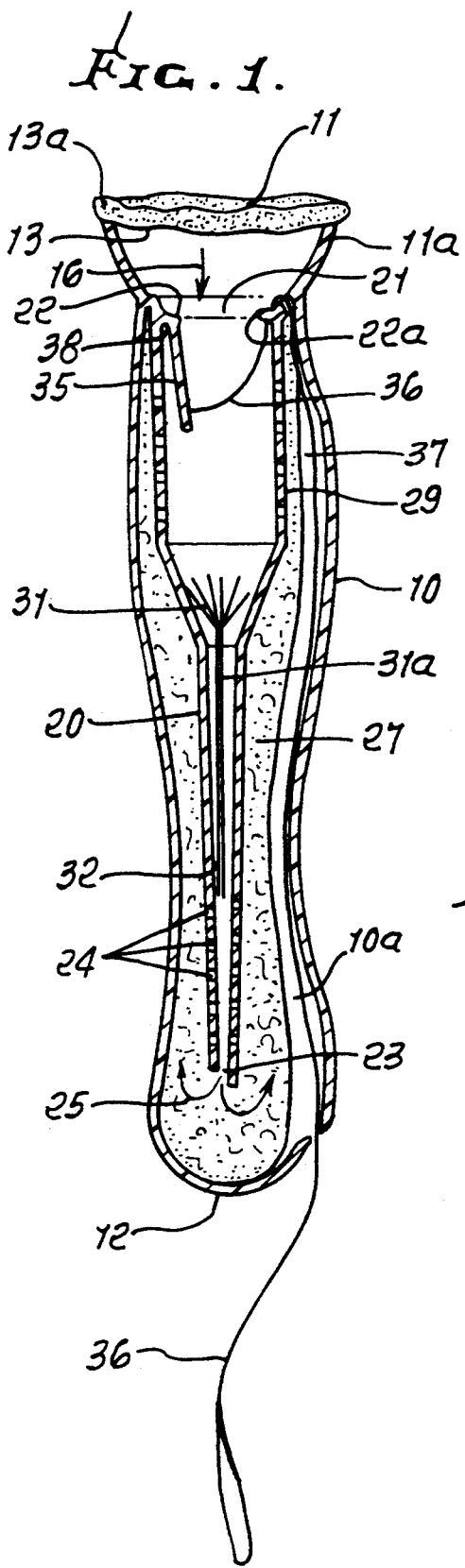
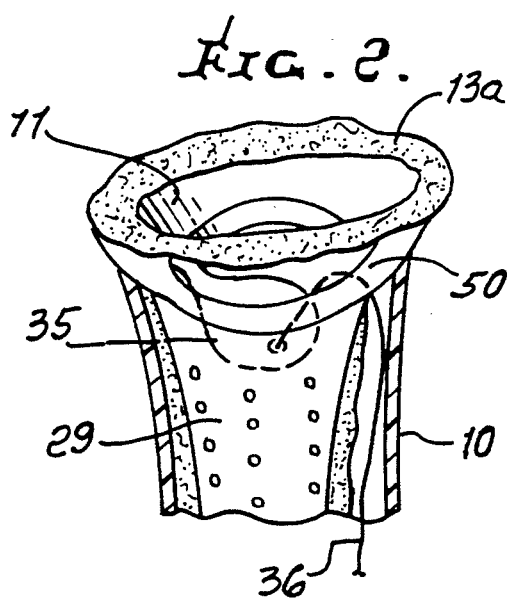
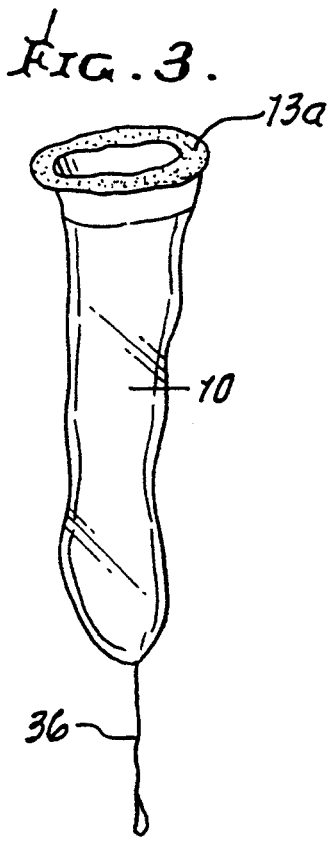
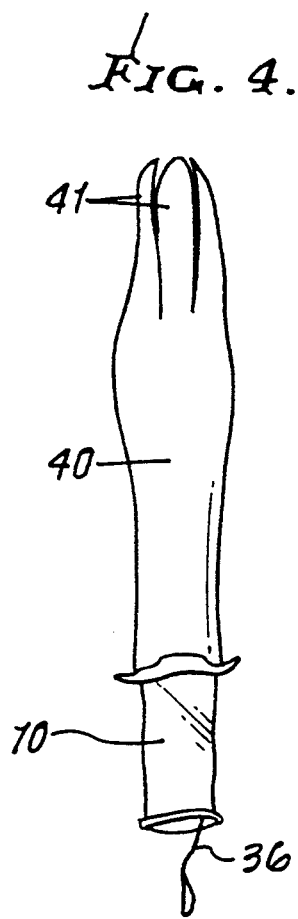

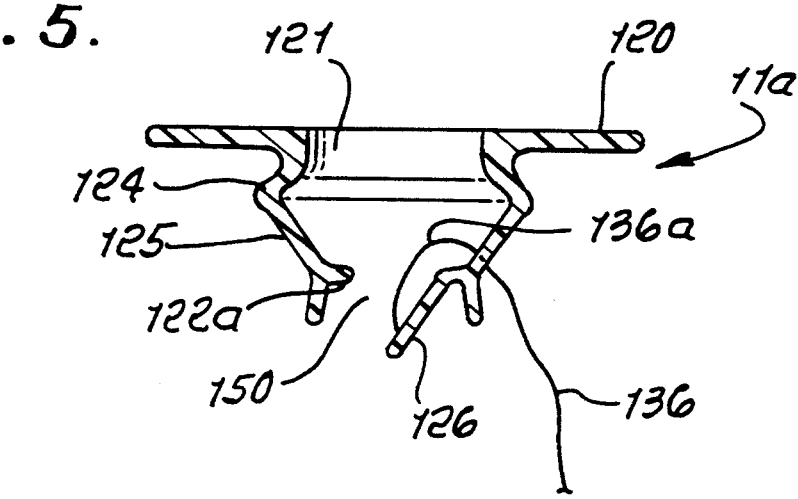
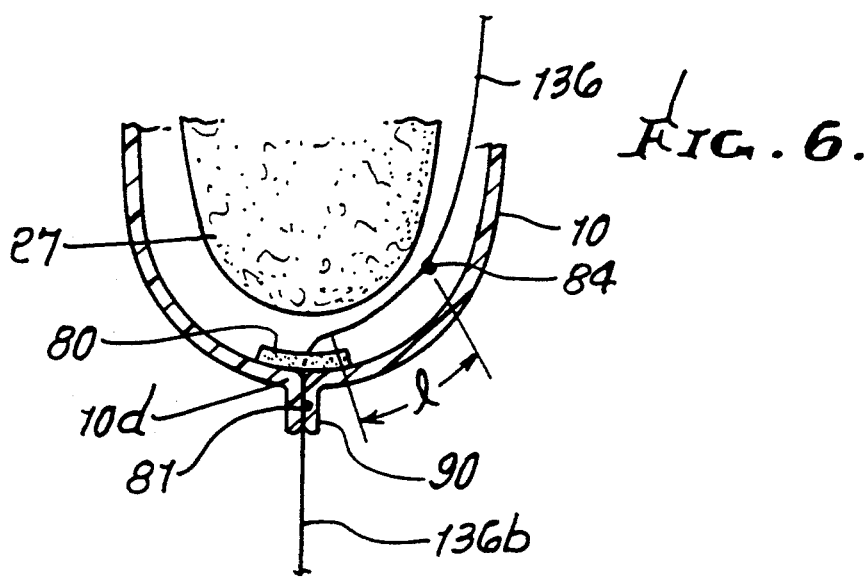
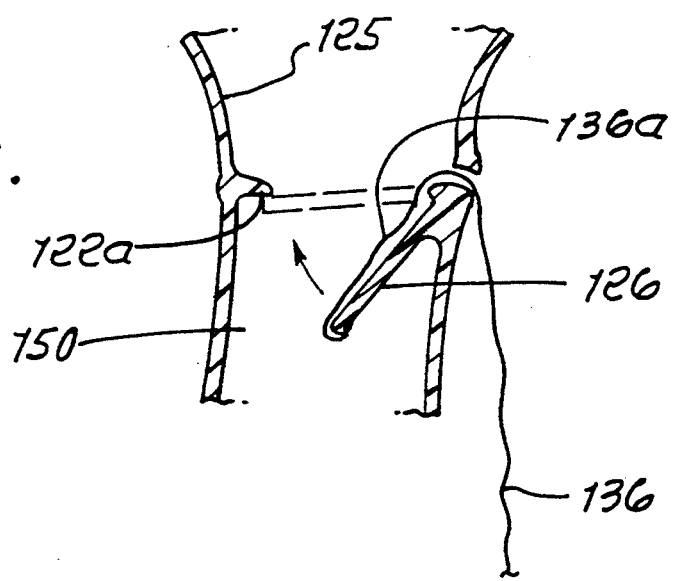

TOXICITY RESISTANT TAMPON STRUCTURE

BACKGROUND OF THE INVENTION

This invention relates generally to flow-controlling tampons, and more specifically to an improved tampon which controls and collects menstrual flow in such manner as to prevent toxic reaction.

In the past, flow collection tampons were found to be objectionable due to toxic reaction, as at tissue surfaces contacted by the collecting flow over periods of time. Also, prior tampons were found objectionable due to flow leakage and contact with the user's hands, as during tampon removal.

There is need for improved tampon apparatus overcoming the above problems and difficulties, as well as providing additional and improved structural and functional features, as well as enhanced or better results, including protection and comfort in use.

SUMMARY OF THE INVENTION

It is a major object to provide improved tampon apparatus which meets the above needs.

Basically, the flow-controlling tampon of the present invention comprises:

a) a generally upright, elongated sheath structure having an open upper end and a closed lower end, the upper end sized to fit about the cervix, b) an inner, elongated, flow-control tube extending generally upright within the sheath, the tube having an upper open end to receive flow via the upper open end of the sheath, and the flow-control tube having lower opening means to pass flow from the tube into the lower interior of the sheath to gradually collect upwardly from the lower interior of the sheath, and about the control tube.

As will be seen, the sheath typically includes a funnel-shaped, upper portion defining the open upper end of the sheath, the funnel-shaped, upper portion having a looping upper edge to fit about the cervix. A moisture absorbent ring seal may be provided at that looping upper edge.

Another object is the provision of moisture absorbent fill material in the lower interior of the sheath and extending about the tube, thereby to receive collected flow near the lower end of the tube, to fill into the sheath from its lower closed end portion, thereby preventing collecting moisture contact with the user's tissue outside the sheath. Such collecting flow may be separated from clot material, as via a clot collection chamber in the upper extent of the flow control inner tube and clot collection mesh may be provided in the clot chamber and therebelow, as will be seen.

Yet another object is the provision of a closure flap within the sheath and proximate the uppermost extent of the tube, and a withdrawal string attached to the flap to urge the flap in a tube-closing direction when the string is pulled downwardly. The user may thereby automatically close the upper end of the sheath upon sheath withdrawal, via pulling of the string. Since the lower end of the sheath is closed at all times, a withdrawal of the tampon apparatus is easily achieved without flow escape to contact the user's hand.

A further object includes the provision of an applicator duct extending about the sheath, and having spreadable flap means at its upper end to pass the sheath upper end relatively upwardly and outwardly, relative to the flap means.

These and other objects and advantages of the invention, as well as the details of an illustrative embodiment, will be more fully understood from the following specification and drawings, in which:

DRAWING DESCRIPTION

FIG. 1 is a vertical section taken through apparatus embodying the invention;

FIG. 2 is a fragmentary section enlarged to show details at the upper end of the sheath;

FIG. 3 is an exterior view of the tampon apparatus sheath;

FIG. 4 is an elevation showing an applicator into which the sheath is receivable;

FIG. 5 is a vertical section through a modified funnel;

FIG. 6 is a vertical section through a modified lower portion of the apparatus; and FIG. 7 is a vertical section through a modified upper portion of the apparatus.

DETAILED DESCRIPTION

FIG. 1 shows the generally vertically elongated sheath structure 10 having an open upper end 11 and a closed lower end 12. The upper end is sized to fit closely over the cervix to collect menstrual flow; it may include a funnel-shaped upper portion 11a defining the open upper end 11. The funnel has a looping upper edge 13 to fit about the cervix; and a moisture absorbent ring seal 13a may be provided at that edge to comfortably engage the cervix and provide a seal to prevent leakage to the area about the sheath. Seal 13a may contain a suitable disinfectant. The funnel directs the collected flow downwardly, as indicated by arrow 16. The sheath consists of material, such as latex, that prevents fluid passage through the sheath wall and bottom end.

An elongated flow-control tube 20 is located within the sheath and is flexible, as is the sheath. The tube 20 has an upper open end 21 to receive downward flow via the upper open end of the sheath, and for that purpose, the tube upper end may be attached to the sheath at ring zone 22. The tube may have an open lower end at 23, and/or side wall perforations at 24 near the tube lower end, to allow escape of collecting flow into the sheath interior at 10a. Accordingly, the flow collects in the sheath lower interior first, and then fills upwardly in direction 25, over time however, the collecting flow is kept from escape from the elongated sheath. Absorbent fill material 27 is preferably located in the sheath lower interior and about the tube, and absorbs the flow, as it fills upwardly.

The tube desirably has an enlarged upper portion 29 defining a clot collection zone or chamber 30 in the sheath upper interior. Clot collecting mesh material 31, may be located in the chamber lower interior to separate clot particles from the liquid flow draining downwardly in the tube lower extent 32, for collection in the sheath. Mesh strands may also extend downwardly at 3a in the tube, to serve as back up for clot collection. By removing clots, the flow into the tube lower end and into the sheath remains open for ensured collection of maximum amount, and without blockage in the flow-control tube.

A closure flap 35 is provided within the sheath and proximate the uppermost extent of the tube, and a withdrawal string is attached to the flap to urge the flap in an upward, tube-closing direction when the string is pulled downwardly. See the string 36 extending from the free end of the flap 35 over the tube edge 50 to the tube exterior, at 37. The flap is hinged at 38 to the tube, at zone 22, whereby, when the user pulls on the string to remove the tampon, the flap closes upwardly toward ring seat 22a to provide a seal against flow escape upwardly during removal.

In FIG. 4, an applicator duct 40 receives the sheath for insertion into the vagina, and separation of the duct from the sheath. Note the spreadable flaps 41 of the duct, via which the sheath emerges, as the duct is pulled back relative to the sheath.

In FIG. 5, a modified funnel 111a consists of very flexible, molded material, such as an elastomer. It has a flange 120 extending about an upper opening 121 that closely fits over the cervix in the vagina. Flange flexibility assures a good seal. The funnel 111a tapers downwardly and outwardly at 124, and then downwardly and inwardly at 125, as in FIG. 1. A flap 126 that extends downwardly and inwardly is to be pulled upwardly by a withdrawal string 136, and toward and against a ring seat 122a, as before. However, as shown in FIG. 7, the string extends at 136a adjacent the flap top, so as not to prevent or block flow of fluid downwardly through the gap 150.

In FIG. 6, the withdrawal string or strand 136 passes downwardly between sheath 10 and tube 20, toward a central lowermost portion 10d of sheath 10. At that zone, the string passes downwardly through a seal 80 and through a lowermost opening 81 to the exterior, at 136b. A knot or other enlargement 84 on the string is positioned on the string at a strength length "1" above the seal. Therefore, the user can pull downwardly on the string, whereby the knot engages the seal to positively push downwardly to withdraw the device from the vagina, via a central and downward force exertion vector. This avoids sideward crumpling or other impediments to device withdrawal.

A tab 90 protrudes downwardly from the sheath, to sealingly pass the string; and it also enables grasping of the tab by a user's finger to pull the device downwardly, as for adjustment while unseated, or as a back-up method for device withdrawal.

We claim:

1. A flow-controlling tampon, comprising
   a) a generally upright enlongated sheath structure having an open upper end and a closed lower end, said upper end sized to fit about the cervix,
   b) an inner, elongated, flow-control tube extending generally upright within said sheath, said tube having an upper open end to receive flow via said upper open end of the sheath, and said flow-control tube having lower opening means to pass flow from the tube into the lower interior of the sheath to gradually collect upwardly from said lower interior of the sheath, and about the control tube,
   c) there being moisture absorbent fill material in the lower interior of the sheath and extending about said tube,
   d) said sheath including a funnel-shaped upper portion defining said open upper end of the sheath, said funnel-shaped upper portion having a looping upper edge to fit about the cervix,
   e) and including a closure flap having hinge support within the sheath and proximate the uppermost extent of said tube, and a withdrawal string attached to said flap to urge the flap in tube-closing direction when the string is pulled downwardly, the flap normally extending within the sheath in a position wherein the flap does not obstruct flow in the tube.

2. The combination of claim 1 including a ring seal at said looping upper edge.

3. The combination of claim 1 wherein said tube has an enlarged upper portion defining a clot collection chamber.

4. The combination of claim 3 including clot collection mesh within the tube and located at the collection chamber.

5. The combination of claim 4 wherein said mesh extends downwardly within the tube from the lower interior of said clot collection chamber.

6. The combination of claim 1 wherein the string extends from said flap to the tube exterior proximate the upper end of said tube, the string then hanging downwardly, along the sheath sideward, interior.

7. The combination of claim 6 including a sealing through port at the bottom of the sheath passing a lower portion of the string.

8. The combination of claim 7 including an enlargement on the string above said port, to engage the surface associated with the sheath, to push the sheath in the direction of string pull downwardly from the sheath.

9. The combination of claim 1 wherein said sheath and tube consist of flexible materials.

10. The combination of claim 9 wherein the sheath consists of latex.

11. The combination of claim 1 including an applicator duct extending about said sheath, and having spreadable flap means at its upper end to pass the sheath upper end relatively upwardly and outwardly, relative to the flap means.

12. The combination of claim 1 wherein said funnel-shaped upper portion is soft, pliable and flexible.

* * * * *